United States Patent

Glombik et al.

Patent Number: 5,874,451
Date of Patent: Feb. 23, 1999

[54] PROPANOLAMINE DERIVATIVES, PROCESSES FOR THEIR PREPARATION, PHARMACEUTICALS COMPRISING THESE COMPOUNDS, AND THEIR USE

[75] Inventors: Heiner Glombik, Hofheim; Alfons Enhsen, Büttelborn; Werner Kramer, Mainz-Laubenheim; Karl-Heinz Baringhaus, Wölfersheim, all of Germany

[73] Assignee: Hoechst Marion Roussel Deutschland GmbH, Frankfurt am Main, Germany

[21] Appl. No.: 53,513

[22] Filed: Apr. 2, 1998

[30] Foreign Application Priority Data

Apr. 4, 1997 [DE] Germany ............... 197 13 865.9
Jan. 26, 1998 [DE] Germany ............... 198 02 530.0

[51] Int. Cl.$^6$ ............... C07D 213/02; C07D 401/02; A61K 31/44
[52] U.S. Cl. ............... 514/357; 514/212; 514/256; 514/314; 514/332; 514/340; 514/357; 540/596; 544/333; 546/176; 546/255; 546/262.7; 546/271.4; 546/334
[58] Field of Search ............... 540/596; 544/333; 546/176, 269.7, 255, 271.4, 334; 514/212, 256, 314, 340, 332, 357, 342

[56] References Cited

FOREIGN PATENT DOCUMENTS

| 0 345 591 A1 | 5/1989 | European Pat. Off. . |
| 0 489 423 A1 | 12/1991 | European Pat. Off. . |
| 0 557 879 A1 | 2/1993 | European Pat. Off. . |
| WO 93/16055 | 8/1993 | WIPO . |

OTHER PUBLICATIONS

International Search Report dated Jul. 10, 1998.
English–language Abstract of EPO 0 345 591 A1 (Derwent Abstract No. 89–365308/198950).

Lyapova, M. et al., "Diastereomers with three neighboring phenyl groups. Part IX. Optical resolution and absolute configurations of 3–amino–1,2,3–triphenylpropanols," Chem. Abs. 99(11) (Sep. 12, 1983), Abstract No. 87735.

Huang, Y. and Hall, I. H., "Hypolipidemic effects of α, β, and γ–alkylaminophenone analogs in rodents," *Eur. J. Med. Chem.* 31:281–290 (1966).

Deutsches Arzneibuch (German Pharmacopeia), 9th ed., 1986, Deutscher Apotheker–Verlag Stuttgart, S. 19. (Table translation provided).

Pirkle, W.H. et al., "Dynamic NMR Studies of Diastereomeric Carbamates: Implications towards the Determination of Relative Configuration by NMR," *J. Org. Chem.*, vol. 44, No. 26, pp. 4891–4896 (1979).

*Primary Examiner*—Zinna Northington Davis
*Attorney, Agent, or Firm*—Finnegan, Henderson, Farabow, Garrett & Dunner, L.L.P.

[57] ABSTRACT

The invention relates to substituted propanolamine derivatives and their acid addition salts.
Propanolamine derivatives of formula I,

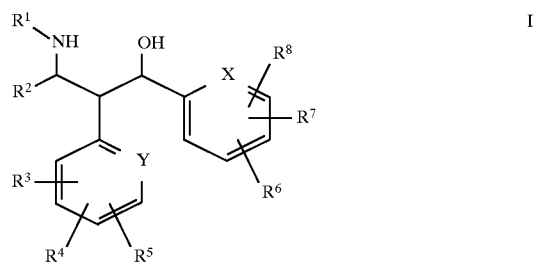

in which $R^1$ to $R^8$ have the meanings indicated in the specification, and their physiologically tolerable salts and processes for their preparation are described. The compounds are suitable, for example, as hypolipidemics.

17 Claims, No Drawings

PROPANOLAMINE DERIVATIVES, PROCESSES FOR THEIR PREPARATION, PHARMACEUTICALS COMPRISING THESE COMPOUNDS, AND THEIR USE

FIELD OF THE INVENTION

The invention relates to substituted propanolamine derivatives and their acid addition salts.

BACKGROUND OF THE INVENTION

Several classes of active compounds have already been described for the treatment of obesity and disorders of lipid metabolism:

polymeric adsorbers, such as, for example, cholestyramine benzothiazepines (WO 93/16055)

bile acid dimers and conjugates EP 0 489 423)

4-amino-2-ureidopyrimidine-5-carboxamides (EP 0 557 879)

The invention is based on the object of making availiable compounds which display a therapeutically utilizable hypolipidemic action.

The invention therefore relates to propanolamine derivatives of the formula I,

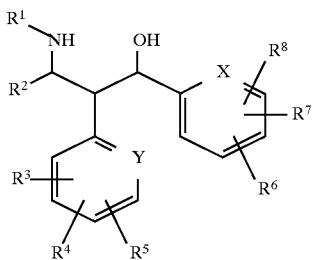

in which $R^1$ and $R^2$ independently of one another are cycloalkyl having 3–8 ring carbon atoms, phenyl, naphthyl, phenanthryl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl or their thieno-, pyridino- or benzo-fused derivatives, it being possible for the cycloalkyl ring, aromatic ring or heteroaromatic ring to be mono- to trisubstituted by fluorine, chlorine, bromine, iodine, OH, $CF_3$, —$NO_2$, CN, ($C_1$-$C_8$)-alkoxy, ($C_1$-$C_8$)-alkyl, $NH_2$, —NH—$R^9$, —N($R^9$)$R^{10}$, CHO, —COOH, —COOR$^{11}$, —(C=O) —$R^{12}$, ($C_1$-$C_6$)-alkyl-OH, ($C_1$-$C_6$)-alkyl(—OH)-phenyl, ($C_1$-$C_6$)-alkyl-$CF_3$, ($C_1$-$C_6$)-alkyl-$NO_2$, ($C_1$-$C_6$)-alkyl-CN, ($C_1$-$C_6$)-alkyl-$NH_2$, ($C_1$-$C_6$)-alkyl-NH—$R^9$, ($C_1$-$C_6$)-alkyl-N($R^9$)$R^{10}$, ($C_1$-$C_6$)-alkyl-CHO, ($C_1$-$C_6$)-alkyl-COOH, ($C_1$-$C_6$)-alkyl-COOR$^{11}$, ($C_1$-$C_6$)-alkyl-(C=O)—$R^{12}$, —O—($C_1$-$C_6$)-alkyl-OH, —O—($C_1$-$C_6$)-alkyl-$CF_3$, —O—($C_1$-$C_6$)-alkyl-$NO_2$, —O—($C_1$-$C_6$)-alkyl-CN, —O—($C_1$-$C_6$)-alkyl-$NH_2$, —O—($C_1$-$C_6$)-alkyl-NH—$R^9$, —O—($C_1$-$C_6$)-alkyl-N($R^9$)$R^{10}$, —O—($C_1$-$C_6$)-alkyl-CHO, —O—($C_1$-$C_6$)-alkyl-COOH, —O—($C_1$-$C_6$)-alkyl-COOR$^{11}$, —O—($C_1$-$C_6$)-alkyl-(C=O)—$R^{12}$, —N—$SO_3H$, —$SO_2$—$CH_3$, —O—($C_1$-$C_6$)-alkyl-O—($C_1$-$C_6$)-alkylphenyl, it being possible in the alkyl radicals for one or more hydrogen(s) to be replaced by fluorine;

$R^3$ to $R^8$ independently of one another are hydrogen, fluorine, chlorine, bromine, iodine, OH, $CF_3$, —$NO_2$, CN, ($C_1$-$C_8$)-alkoxy, ($C_1$-$C_8$)-alkyl, $NH_2$, —NH—$R^9$, —N($R^9$)$R^{10}$, CHO, —COOH, —COOR$^{11}$, —(C=O) —$R^{12}$, it being possible in the alkyl radicals for one or more hydrogen(s) to be replaced by fluorine;

$R^9$ to $R^{12}$ independently of one another are hydrogen, ($C_1$-$C_8$)-alkyl;

X is CH, NH;

Y is CH, NH;

with the proviso that the radicals $R^1$, $R^2$, X and Y do not simultaneously have the following meaning:

$R^1$ is phenyl;

$R^2$ is phenyl;

X is CH;

Y is CH;

and their physiologically tolerable acid addition salts.

Preferred compounds of formula I are those in which one or more radical(s) has or have the following meaning:

$R^1$ and $R^2$ independently of one another are cycloalkyl having 3–8 ring carbon atoms, phenyl, naphthyl, thienyl, furyl, pyrimidyl, thiazolyl, imidazolyl, phthalimidyl, quinolyl, piperazinyl, tetrazolyl, triazolyl, oxazolyl or their thieno-, pyridino- or benzo-fused derivatives, it being possible for the cycloalkyl ring, aromatic ring or heteroaromatic ring to be mono- to tri-substituted by fluorine, chlorine, bromine, OH, $CF_3$, —$NO_2$, CN, ($C_1$-$C_8$)-alkoxy, ($C_1$-$C_8$)-alkyl, $NH_2$, —NH—$R^9$, —N($R^9$)$R^{10}$, —COOH, —COOR$^{11}$, —(C=O)—$R^{12}$, it being possible in the alkyl radicals for one or more hydrogen(s) to be replaced by fluorine;

$R^3$ to $R^8$ independently of one another are hydrogen, fluorine, chlorine, bromine, OH, $CF_3$, —$NO_2$, CN, ($C_1$-$C_8$)-alkoxy, ($C_1$-$C_8$)-alkyl, $NH_2$, —NH—$R^9$, —N($R^9$)$R^{10}$, —COOH, —COOR$^{11}$, —(C=O)—$R^{12}$, it being possible in the alkyl radicals for one or more hydrogen(s) to be replaced by fluorine;

$R^9$ to $R^{12}$ independently of one another are hydrogen, ($C_1$-$C_8$)-alkyl;

X is CH, NH;

Y is CH, NH;

with the proviso that the radicals $R^1$, $R^2$, X and Y do not simultaneously have the following meaning:

$R^1$ is phenyl;

$R^2$ is phenyl;

X is CH;

Y is CH;

and their physiologically tolerable acid addition salts.

Particularly preferred compounds of formula I are those in which one or more radical(s) has or have the following meaning:

$R^1$ is pyridyl, pyrimidyl, thienyl, thiazolyl, it being possible for the heteroaromatic ring to be mono- to trisubstituted by fluorine, chlorine, bromine, iodine, OH, $CF_3$, —$NO_2$, CN, ($C_1$-$C_8$)-alkoxy, ($C_1$-$C_8$)-alkyl, $NH_2$, —NH—$R^9$, —N($R^9$)$R^{10}$, CHO, —COOH, —COOR$^{11}$, —(C=O)—$R^{12}$;

$R^2$ is phenyl, it being possible for the aromatic ring to be mono- to trisubstituted by fluorine, chlorine, bromine, OH, $CF_3$, —$NO_2$, CN, ($C_1$-$C_8$)-alkoxy, ($C_1$-$C_8$)-alkyl, $NH_2$, —NH—$R^9$, —N($R^9$)$R^{10}$, —COOH, —COOR$^{11}$, —(C=O)—$R^{12}$;

$R^3$ to $R^8$ independently of one another are hydrogen, fluorine, chlorine, bromine, iodine, OH, $CF_3$, —$NO_2$, CN, ($C_1$-$C_8$)-alkoxy, ($C_1$-$C_8$)-alkyl, $NH_2$, —NH—$R^9$, —N($^9$)$R^{10}$, CHO, —COOH, —COOR$^{11}$, —(C=O)—

$R^{12}$, it being possible in the alkyl radicals for one or more hydrogen(s) to be replaced by fluorine;

$R^9$ to $R^{12}$ independently of one another are hydrogen, $(C_1-C_8)$-alkyl;

X is CH;

Y is NH;

and their physiologically tolerable acid addition salts.

Physiologically tolerable acid addition salts are understood as meaning readily water-soluble, soluble and less soluble compounds according to the definition in *Deutschen Arzneibuch* ("German Pharmacopeia", 9th Edition 1986, Official Edition, Deutscher Apotheker-Verlag Stuttgart), page 19. The hydrochlorides and sulfates of the compounds are preferred.

The invention relates both to isomer mixtures of formula I, and to the pure enantiomers of formula I.

The invention furthermore relates to processes for the preparation of propanolamine derivatives of formula I.

Process A:

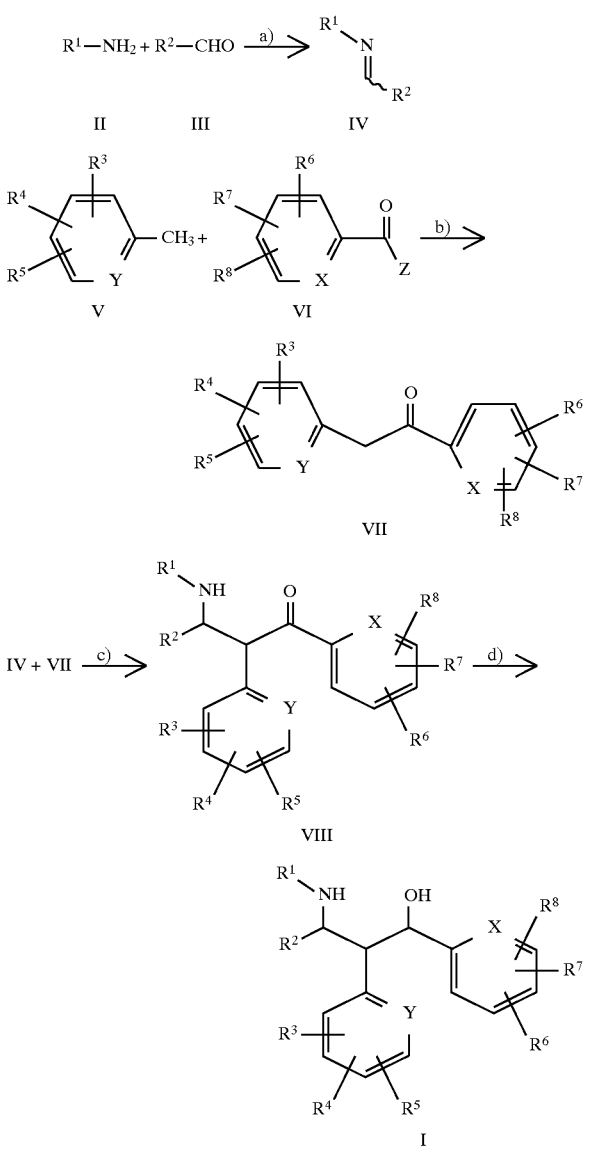

Process B:

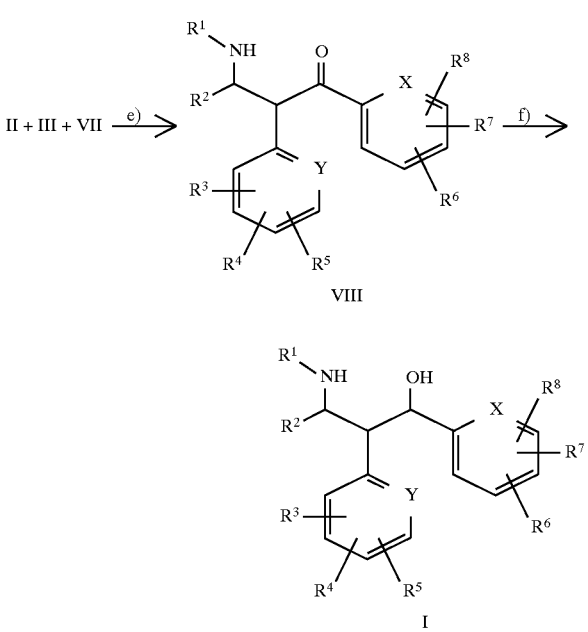

Process A for the preparation of the compounds of formula I comprises a) preparing imines substituted by $R^1$ and $R^2$ and which are unknown from the literature, $R^1$ and $R^2$ having the meaning indicated for formula I, following literature processes, from amines of type II and aldehydes of type III. To do this, for example, the amine II and the aldehyde III are reacted in undiluted form or in a suitable solvent such as ethanol, toluene or acetic acid with or without addition of an acid, e.g. p-toluenesulfonic acid, at temperatures of 20°–150° C.

Keto compounds of formula VII substituted by radicals $R^3$ to $R^8$, $R^3$ to $R^8$ having the meaning indicated for formula I, are prepared by processes known from the literature or following such processes. Thus, for example, picoline derivatives V are metalated with a suitable base, such as n-butyllithium, and reacted in tetrahydrofuran or another suitable solvent with the corresponding carboxylic acid derivatives VI, e.g. present as carboxylic acid dialkylamides or esters, at temperatures between –80° and 20° C.

Compounds of type VIII are obtained by reacting imines of type IV and ketones of type VII, in each case substituted by radicals $R^3$ to $R^8$, $R^3$ to $R^8$ having the meaning indicated for formula I. This reaction can be carried out, for example, by mixing of the two compounds in diluted form, without solvent, and subsequent heating, or in a suitable solvent such as ethanol, toluene, diglyme or tetradecane, at temperatures from 20° C. to 150° C. (c).

The keto compounds of type VIII are reduced to hydroxy compounds of type I in a suitable solvent, such as, for example, methanol, THF or THF/water using $NaBH_4$ or another suitable reductant, at temperatures between –30° and +40° C., it being possible for compound I to be substituted by the radicals $R^3$ to $R^8$ and $R^3$ to $R^8$ having the meaning indicated for formula I (d).

The compounds of formula I are obtained by the above-described reduction as isomer mixtures. Different isomers can be separated from one another by fractional crystallization or by column chromatography. The pure enantiomers can be obtained from the racemates of the compounds of formula I by chromatography on chiral column material or by processes known from the literature using optically active auxiliary reagents, such as described in *J. Org. Chem.* 44, 4891 (1979). In addition, the compounds of formula I can be readily converted into their physiologically tolerable acid addition salts by known processes.

Process B for the preparation of the compounds of formula I comprises not preparing and isolating the imine compound IV as process A, but preparing the compounds of type VIII, substituted by the radicals $R^3$ to $R^8$, in a three-component reaction from ketones VII, amines II and aldehydes III. To do this, these three components are reacted in undiluted form or in a suitable solvent, such as ethanol, tetradecane or toluene, at temperatures from 20° C. to 150° C. (e). The compounds VIII are reduced, as described for process A, to the compounds of formula I (f), it being possible to employ the compounds VIII as purified ketones, but also as crude products from the reaction described above.

The present invention also relates to pharmaceutical preparations which, in addition to nontoxic, inert, pharmaceutically suitable excipients, contain one or more active compounds according to the invention or which consist of one or more active compounds according to the invention, and to processes for the production of these preparations.

Nontoxic, inert, pharmaceutically suitable excipients are pharmaceutically acceptable solid, semisolid or liquid diluents, fillers and formulation auxiliaries of any type, which after mixing with the active compound bring this into a form suitable for administration.

Suitable administration forms of the compounds according to the invention are, for example, tablets, coated tablets, capsules, pills, aqueous solutions, suspensions and emulsions, where appropriate sterile injectable solutions, nonaqueous emulsions, suspensions and solutions, sprays and also preparation forms having protracted release of active compound.

The therapeutically active compounds should be present in the above mentioned pharmaceutical preparations expediently in a concentration from approximately 0.1 to 99.0, preferably from 0.5 to 70.0, percent by weight of the total mixture.

The administration concentrations for solutions and also aerosols in the form of sprays are in general 0.1 to 20, preferably 0.5 to 5, percent by weight.

Apart from the active compounds according to the invention, the abovementioned pharmaceutical preparations can also contain other pharmaceutically active compounds.

The abovementioned pharmaceutical preparations are prepared in a customary manner by known methods, e.g. by mixing the active compound(s) with the excipient(s).

The active compounds or the pharmaceutical preparations can be administered orally, parenterally, intraperitoneally and/or rectally.

The compounds of the present invention and their salts, which are utilizable, for example, as hypolipidemics, can be used for the production of pharmaceutical preparations which contain an efficacious amount of the active substance together with excipients and which are suitable for enteral and parenteral administration. Tablets or capsules (gelatin capsules) are preferably used which contain the active compound together with diluents or excipients, e.g. lactose, dextrose, cane sugar, mannitol, sorbitol, cellulose, various types of starch and/or glycine, and lubricants such as silica, talc, stearic acid or its salts, such as magnesium or calcium stearate, and/or polyethylene glycol. Tablets also contain binders such as magnesium carbonate, magnesium aluminum silicate, starch, gelatine, tragacanth, methylcellulose, sodium carboxymethylcellulose and/or polyvinylpyrrolidone and, if required, colorants, flavorings and sweeteners. Injectable solutions are preferably isotonic aqueous solutions or suspensions, which can be sterilized and can contain auxiliaries, such as preservatives, stabilizers, wetting agents and/or emulsifiers, solubilizers, salts for regulating the osmotic pressure and/or buffer substances. The pharmaceutical preparations according to the invention, which if desired can contain further pharmacologically active substances, are produced, for example, by means of conventional mixing, granulating and sugar-coating processes and contain 0.1% to 80%, preferably approximately 5% to approximately 65%, of the active compound.

Oral administration takes place in pharmaceutically customary preparations, for example in the form of tablets, coated tablets or capsules which contain, for example, per daily dose 5 to 1000 mg, preferably 20 to 200 mg, of the active compound as a mixture with a customary excipient and/or constituent, it being possible to give individual doses of 5 to 200 mg, preferably one to three times daily.

However, it may be necessary to depart from the doses mentioned, namely depending on the type and the body weight of the subject to be treated, the nature and severity of the disorder, the type of preparation and the administration of the medicament, and the time or interval within which administration takes place. Thus in some cases it may be adequate to manage with less than the abovementioned amount of active compound, while in other cases the abovementioned amount of active compound must be exceeded. The optimal dose and type of administration of the active compounds necessary in each case can be established by any person skilled in the art on account of his/her expert knowledge.

The compounds of formula I and their physiologically tolerable salts are ideal pharmaceuticals for the treatment of disorders of lipid metabolism, in particular of hyperlipidemia. The compounds of formula I are also suitable for affecting the serum cholesterol level and for the prevention and treatment of arteriosclerotic symptoms. The following findings confirm the pharmacological activity of the compounds according to the invention.

The biological testing of the compounds according to the invention was carried out by determination of the inhibition of the [$^3$H]-taurocholate uptake in brush-border membrane vesicles of the ileum of rabbits. The inhibition test was carried out as follows:

1. Preparation of brush-border membrane vesicles from the ileum of rabbits

The preparation of brush-border membrane vesicles from the intestinal cells of the small intestine was carried out using the so-called $Mg^{2+}$ precipitation method. Male New Zealand rabbits (2 to 2.5 kg body weight) were sacrificed by intravenous injection of 0.5 ml of T61®, an aqueous solution of 2.5 mg of tetracaine HCl, 100 mg of embutramide and 25 mg of mebezonium iodide. The small intestine was removed and rinsed with ice-cold physiological saline solution. The terminal 7/10 of the small intestine (measured in the oral-rectal direction, i.e. the terminal ileum, which contains the active $Na^+$-dependent bile acid transport system) were used for the preparation of the brush-border membrane vesicles. The intestines were frozen in plastic bags under nitrogen at −80° C. For the preparation of the membrane vesicles, the frozen intestines were thawed at 30° C. in a water bath. The mucosa were scraped off and suspended in 60 ml of ice-cold 12 mM Tris/HCl buffer (pH 7.1)/300 mM mannitol, 5 mM EGTA/10 mg/L of phenylmethylsulfonyl fluoride/L mg/L of trypsin inhibitor from soybeans (32 U/mg)/0.5 mg/L trypsin inhibitor from bovine lung (193 U/mg)/5 mg/L of bacitracin. After diluting to 300 ml with ice-cold distilled water, homogenization was carried out with an Ultraturrax (18-rod, IKA Werk Staufen, Germany) for 3 minutes at 75% max. power with ice-cooling. After addition of 3 ml of 1M $MgCl_2$ solution (final concentration 10 mM), the homogenizate was allowed to stand at 0° C. for exactly 1 minute. By addition of $Mg^{2+}$, the cell membranes aggregate and precipitate with the exception of the brush-border membranes. After centrifugation at 3000×g for 15 minutes (5000 rpm, SS-34 rotor), the precipitate was discarded and the supernatant which contains the brush-border membranes was centrifuged at 48000×g for 30 minutes (20000 rpm, SS-34 rotor). The supernatant was discarded and the precipitate was re-homogenized in 60 ml of 12 mM Tris/HCl buffer (pH 7.1)/60 mM mannitol, 5 mM EGTA using a Potter Elvejhem homogenizer (Braun Melsungen, 900 rpm, 10 strokes). After addition of 0.1 ml of 1M $MgCl_2$ solution and an incubation time of 15 minutes at 0° C., centrifugation at 3000×g was again carried out for 15 minutes. The supernatant was then centrifuged again at 48000×g for 30 minutes (20000 rpm, SS-34 rotor). The precipitate was taken up in 30 ml of 10 mM Tris/HEPES buffer (pH 7.4)/300 mM mannitol and homogeneously resuspended by 20 strokes in a Potter Elvejhem homogenizer at 1000 rpm. After centrifugation at 48000×g for 30 minutes (20000 rpm, SS-34 rotor), the prcipitate was taken up in 0.5 to 2 ml of Tris/HEPES buffer (pH 7.4)/280 mM mannitol (final concentration 20 mg/ml) and resuspended with the aid of a tuberculin syringe having a 27 gauge needle. The vesicles were either used for transport investigations immediately after preparation or stored in liquid nitrogen at −196° C. in 4 mg aliquots.

2. Inhibition of the $Na^+$-dependent [$^3$]-taurocholate absorption in brush-border membrane vescles of the ileum The absorption of substrates in the brush-border membrane vesicles described above was determined by means of the so-called membrane filtration technique. 10 μl of the vesicle suspension (100 μg of protein) were pipetted as drops onto the wall of a polystyrene incubation tube (11×70 mm) which contained the incubation medium with the appropriate ligands (90 μl). The incubation medium contained 0.75 μl=0.75 μCi of [$^3$H(G)]-taurocholate (specific activity: 2.1 Ci/mmol)/0.5 μl of 10 mM taurocholate/8.75 μl of sodium transport buffer (10 mM Tris/HEPES (pH 7.4)/ 100 mM mannitol/100 mM NaCl) (Na-T-B) or 8.75 μl of potassium transport buffer (10 mM tris/HEPES (pH 7.4)/100 mM mannitol/100 mM KCl) (K-T-B) and 80 μl of the inhibitor solution concerned, dissolved in Na-T-buffer or K-T-buffer depending on the experiment. The incubation medium was filtered through a polyvinylidene fluoride membrane filter (SYHV LO 4NS, 0.45 μm, 4 mm diameter, Millipore, Eschborn, Germany). Transport measurement was started by mixing the vesicles with the incubation medium. The concentration of taurocholate in the incubation batch was 50 μM. After the desired incubation time (customarily 1 minute), the transport was stopped by addition of 1 ml of ice-cold stop solution (10 mM tris/HEPES, (pH 7.4)/150 mM KCl). The resulting mixture was immediately filtered off under a vacuum of 25 to 35 mbar through a membrane filter of cellulose nitrate (ME 25, 0.45 μm, 25 mm diameter, Schleicher & Schuell, Dassell, Germany). The filter was washed with 5 ml of ice-cold stop solution.

For measurement of the absorption of the radiolabeled taurocholate, the membrane filter was dissolved using 4 ml of the scintillator Quickszint 361 (Zinsser Analytik GmbH, Frankfurt, Germany) and the radioactivity was measured by liquid scintillation measurement in a TriCarb 2500 measuring apparatus (Canberra Packard GmbH, Frankfurt, Germany). The measured values were obtained as dpm (decompositions per minute) after calibration of the apparatus with the aid of standard samples and after correction for any chemiluminescence present.

The control values were in each case determined in Na-T-B and K-T-B. The difference between the absorption in Na-T-B and K-T-B gave the $Na^+$-dependent transport fraction. The $IC_{50}$ $Na^+$ was designated as that concentration of inhibitor at which the $Na^+$-dependent transport fraction was inhibited by 50%—relative to control.

The pharmacological data comprise a series of tests in which the interaction of the compounds according to the invention with the intestinal bile acid transport system was investigated in the terminal small intestine. The results are summarized in Table 1.

Table 1 shows measurements of the inhibition of the [$^3$H]-taurocholate absorption in brush-border membrane vesicles of the ileum of rabbits. The quotients of the $IC_{50}Na$ values of the reference substance and taurochenodeoxycholate (TCDC) and the respective test substance are indicated.

TABLE 1

| Compounds from Example | $\dfrac{IC_{50Na} - TCDC\ [\mu mol]}{IC_{50Na}\ \text{substance}\ [\mu mol]}$ |
|---|---|
| 6 | 0.10 |
| 10 | 0.36 |
| 32 | 0.29 |
| 36 | 0.22 |
| 61 | 0.20 |
| 70 | 0.27 |
| 72 | 0.28 |
| 83 | 0.22 |
| 86 | 0.24 |
| 101 | 0.23 |

The following Examples serve to illustrate the invention in greater detail without restricting the latter to products and embodiments described in the Examples.

EXAMPLE 1 a.

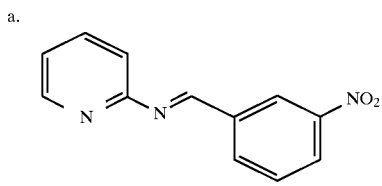

0.7 g of p-toluenesulfonic acid was added to a solution of 25 g (266 mmol) of 2-aminopyridine and 40 g (265 mmol) of 3-nitrobenzaldehyde in 300 ml of toluene and the mixture was heated under reflux for 6 h. After cooling, half of the solvent was stripped off in vacuo and the residue was allowed to stand overnight. The resulting precipitate was filtered off with suction, washed with cold toluene and dried in vacuo. By subsequent recrystallization from n-heptane/ethyl acetate 2:1, 48.8 g (81%) of imine were obtained.

$C_{12}H_9N_3O_2$ (227.2) MS (FAB) 228.2 M+H$^+$ b.

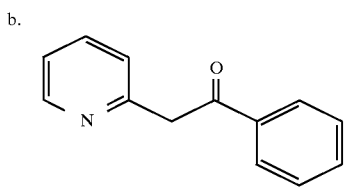

250 ml of n-butyllithium (15% in hexane) were added dropwise at −55° C. to a solution of 50 g (0.54 mol) of 2-picoline in 770 ml of tetrahydrofuran and the mixture was stirred for 10 min. It was then warmed to 0° C. and, after a further 30 min, cooled to −55° C. A solution of 77 g (0.52 mol) of N,N-dimethylbenzamide in 570 ml of tetrahydrofuran was then slowly added dropwise. After the addition, the mixture was warmed to room temperature and stirred for 1 h. After the addition of 500 ml of water and 35 ml of conc. HCl, the organic phase was separated off and the aqueous phase was extracted 2× with ethyl acetate. After drying over MgSO$_4$, the extract was concentrated in vacuo and the residue was distilled in a high vacuum. Boiling point 134°–136° C./0.3 mbar. Yield: 47.5 g (47%) of ketone.

$C_{13}H_{11}NO$ (197.2) MS (FAB) 198.1 M+H$^+$ c.

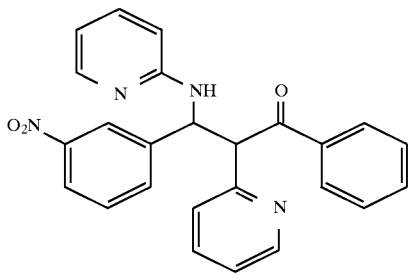

5.8 g (25.5 mmol) of imine from Example 1a and 5.0 g (25.4 mmol) of ketone from Example 1b were well mixed and warmed on a steam bath. After about 20 min, the mixture began to melt and crystallized on further warming. After cooling, the residue was heated to boiling in 200 ml of ethyl acetate, cooled, and the precipitate was filtered off with suction and dried in vacuo. Yield 6.7 g (62%)

$C_{25}H_{20}N_4O_3$ (424.2) MS (FAB) 425.2 M+H$^+$ d.

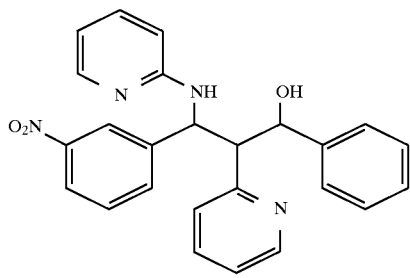

3.0 g (7.1 mmol) of keto compound from Example 1c were dissolved in 50 ml of THF/water 10:1, treated with 1.35 g (35.7 mmol) of sodium borohydride and stirred at room temperature for 1 h. Using 2N HCl, the mixture was brought to pH 1 and stirred at 50° C. for 30 min. After cooling, the reaction mixture was rendered basic using 2N NaOH and extracted 2× with ethyl acetate. The organic phases were dried over MgSO$_4$ and concentrated. The residue was chromatographed on silica gel using n-heptane/ethyl acetate 6:4. By this means, 2 racemic compounds were obtained as the product.

1st fraction: 1.26 g (42%) of nonpolar racemate, $C_{25}H_{22}N_4O_3$ (426.2) MS (FAB) 427.2 M+H$^+$; 2nd fraction: 1.15 g (38%) of polar racemate, $C_{25}H_{22}N_4O_3$ (426.2) MS (FAB) 427.2 M+H$^+$.

e.

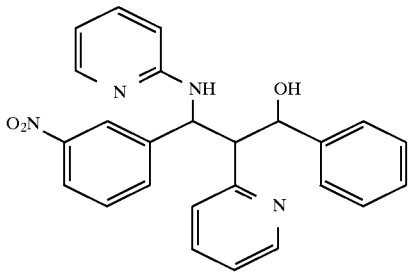

50 mg of the nonpolar racemate from Example 1d were separated into the constituent enantiomers by preparative HPLC. Separation was carried out by means of a CSP Chiralpak column (Daicel, Düsseldorf) using n-hexane/2-propanol 50:10+0.1% diethylamine as eluent. 20 mg of the (−)-enantiomer were obtained as a 1st fraction and 20 mg of the (+)-enantiomer as a 2nd fraction.

f.

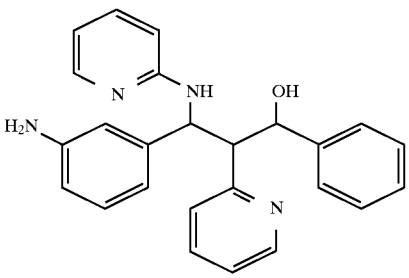

1.0 g (2.34 mmol) of the nonpolar racemate from Example 1d was dissolved in 200 ml of methanol and hydrogenated at room temperature under an H$_2$ atmosphere using about 20 mg of Pd/C 10% for 3 h. The catalyst was filtered off and the solution was evaporated. The residue was chromatographed on silica gel using ethyl acetate/n-heptane 4:1.

Yield: 680 mg (73%) of amino compound, $C_{25}H_{24}N_4O$ (396.2) MS (FAB) 397.3 M+H$^+$.

g.

From 2.0 g (4.69 mmol) of the polar racemate from Example 1d, 1.2 g (65%) of the corresponding amino compound were obtained by the process described for Example 1f.

$C_{25}H_{24}N_4O$ (396.2) MS (FAB) 397.2 M+H$^+$

EXAMPLE 2 a.

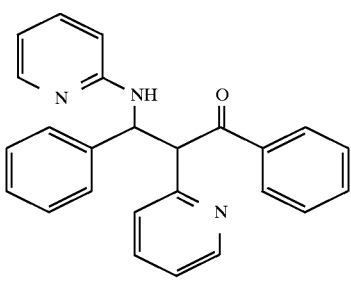

78.8 g (0.4 mol) of ketone from Example 1b, 37.6 g (0.4 mol) of 2-aminopyridine and 21.2 g (0.4 mol) of benzaldehyde were dissolved in 1 l of ethanol and the solution was heated under reflux for 1.5 h with vigorous stirring. It was then additionally stirred for 4 h and allowed to stand overnight. The precipitate was filtered off with suction, washed with a little ethanol and dried in vacuo. Yield 134 g (88%).

$C_{25}H_{21}N_3O$ (379.2) MS (FAB) 380.1 M+H$^+$ b.

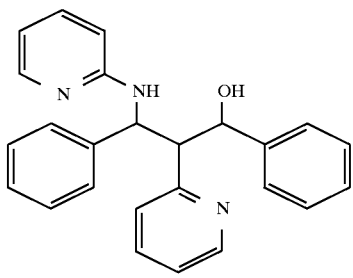

56.9 g (0.15 mol) of ketone from Example 2a were suspended in 1 l of methanol and slowly added in portions to 60 g of NaBH$_4$ in 100 ml of water; temperature rise from 22° C. to 34° C. The alcohol was stripped off in vacuo, and the residue was treated with about 200 ml of water and extracted 3× with ethyl acetate. The organic phases were dried and evaporated. The residue was chromatographed on silica gel using n-heptane/ethyl acetate 2:1. Two racemic compounds were obtained.

1st fraction: 43 g (75%) of nonpolar racemate, $C_{25}H_{23}N_3O$ (381) MS (FAB) 382 M+H$^+$; 2nd fraction: 14 g (24%) of polar racemate, $C_{25}H_{23}N_3O$ (381) MS (FAB) 382 M+H$^+$.

c.

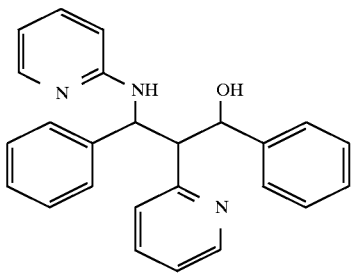

100 mg of the nonpolar racemate from Example 2b were resolved by the process described in Example 1e. Using n-hexane/2-propanol 25:10+0.1% diethylamine as an eluent, 40 mg of the (−)-enantiomer were obtained as a 1st fraction and 30 mg of the (+)-enantiomer as a 2nd fraction.

EXAMPLE 4

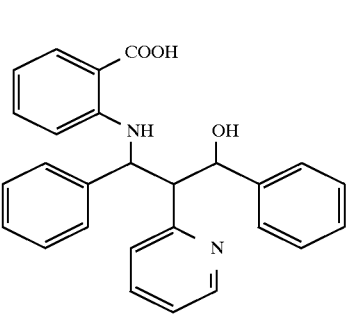

The nonpolar racemate Example 48 in Table 2 was prepared analogously to Example 2, 160 mg (0.36 mmol) of this methyl ester were dissolved in 20 ml of ethanol, treated with 1.6 ml of 2N aqueous NaOH solution and stirred at room temperature for 40 h. The solvent was then completely removed, the residue was dissolved in water and the solution was adjusted to pH 6.5 using 2N hydrochloric acid. It was extracted 2× with 50 ml of ethyl acetate, and the organic phases were dried and concentrated. Chromatography of the residue on silica gel using n-heptane/ethyl acetate 1:1 afforded 110 mg (71%) of product.

$C_{27}H_{24}N_2O_3$ (424.2) FAB 425.2 M+H$^+$

Starting from the corresponding starting compounds, the examples of Tables 1 to 5 were obtained analogously to the processes described for Examples 1 to 4.

TABLE 1

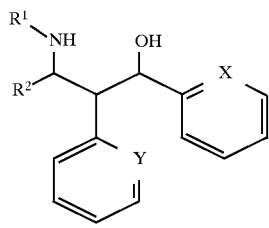

| Example | R$^1$ | R$^2$ | X | Y | Empirical formula (molecular mass) | MS (FAB) |
|---|---|---|---|---|---|---|
| 5 | phenyl | phenyl | CH | N | nonp. rac. $C_{26}H_{24}N_2O$ (380.2) | 381 M + H$^+$ |
| 6 | phenyl | phenyl | CH | N | pol. rac. $C_{26}H_{24}N_2O$ (380.2) | 381 M + H$^+$ |

TABLE 1-continued

[Structure: R¹-NH and R² on one carbon; adjacent carbon with OH and aryl group X; middle carbon has Y-aryl substituent]

| Example | R¹ | R² | X | Y | | Empirical formula (molecular mass) | MS (FAB) |
|---|---|---|---|---|---|---|---|
| 7 | 2-pyridyl | phenyl | CH | CH | nonp. rac. | $C_{26}H_{24}N_2O$ (380.2) | 381 M + H⁺ |
| 8 | 3-pyridyl | phenyl | CH | N | nonp. rac. | $C_{25}H_{23}N_3O$ (381.2) | 382 M + H⁺ |
| 9 | 3-pyridyl | phenyl | CH | N | pol. rac. | $C_{25}H_{23}N_3O$ (381.2) | 382 M + H⁺ |
| 10 | 2-pyridyl | 3-thienyl | CH | N | pol. rac. | $C_{23}H_{21}N_3OS$ (387) | 388 M + H⁺ |
| 11 | 2-pyrimidyl | phenyl | CH | N | nonp. rac | $C_{24}H_{22}N_4O$ (382.2) | 383 M + H⁺ |
| 12 | 2-pyrimidyl | phenyl | CH | N | pol. rac. | $C_{24}H_{22}N_4O$ (382.2) | 383 M + H⁺ |
| 13 | 2-pyridyl | 2-pyridyl | CH | N | nonp. rac. | $C_{24}H_{22}N_4O$ (382.2) | 383 M + H⁺ |
| 14 | 2-pyridyl | 2-pyridyl | CH | N | pol. rac. | $C_{24}H_{22}N_4O$ (382.2) | 383 M + H⁺ |
| 15 | 2-pyridyl | 3-pyridyl | CH | N | nonp. rac. | $C_{24}H_{22}N_4O$ (382.2) | 383 M + H⁺ |
| 16 | 2-pyridyl | phenyl | N | N | nonp. rac. | $C_{24}H_{22}N_4O$ (382.2) | 383 M + H⁺ |
| 17 | 2-pyridyl | phenyl | N | N | pol. rac. | $C_{24}H_{22}N_4O$ (382.2) | 383 M + H⁺ |

TABLE 2

[Structure: R¹-NH-CH(phenyl)-CH(2-pyridyl)-CH(OH)(phenyl)]

| Example | R¹ | | Empirical formula (molecular mass) | MS (FAB) |
|---|---|---|---|---|
| 18 | 2-(3-nitropyridyl) | nonp. rac. | $C_{25}H_{22}N_4O_3$ (426.2) | 427.2 M + H⁺ |
| 19 | 2-(3-nitropyridyl) | pol. rac. | $C_{25}H_{22}N_4O_3$ (426.2) | 427.2 M + H⁺ |
| 20 | 2-(3-aminopyridyl) | nonp. rac. | $C_{25}H_{24}N_4O$ (396.2) | 397.3 M + H⁺ |
| 21 | 2-(3-aminopyridyl) | pol. rac. | $C_{25}H_{24}N_4O$ (396.2) | 397.3 M + H⁺ |
| 22 | 2-(5-nitropyridyl) | nonp. rac. | $C_{25}H_{22}N_4O_3$ (426.2) | 427.1 M + H⁺ |
| 23 | 2-(5-nitropyridyl) | pol. rac. | $C_{25}H_{22}N_4O_3$ (426.2) | 427.1 M + H⁺ |
| 24 | 2-(5-aminopyridyl) | nonp. rac. | $C_{25}H_{24}N_4O$ (396.2) | 397.1 M + H⁺ |
| 25 | 2-(3-hydroxypyridyl) | 1st rac. | $C_{25}H_{23}N_3O_2$ (397.2) | 398 M + H⁺ |
| 26 | 2-(3-hydroxypyridyl) | 2nd rac. | $C_{25}H_{23}N_3O_2$ (397.2) | 398 M + H⁺ |
| 27 | 2-(3-hydroxypyridyl) | 3rd rac. | $C_{25}H_{23}N_3O_2$ (397.2) | 398 M + H⁺ |
| 28 | 2-(3-benzyloxypyridyl) | 1st rac. | $C_{32}H_{29}N_3O_2$ (487.3) | 488 M + H⁺ |
| 29 | 2-(3-benzyloxypyridyl) | 2nd rac. | $C_{32}H_{29}N_3O_2$ (487.3) | 488 M + H⁺ |
| 30 | 2-(3-benzyloxypyridyl) | 3rd rac. | $C_{32}H_{29}N_3O_2$ (487.3) | 488 M + H⁺ |
| 31 | 2-(5-methoxypyridyl) | nonp. rac. | $C_{26}H_{25}N_3O_2$ (411.2) | 412 M + H⁺ |
| 32 | 2-(5-methoxypyridyl) | pol. rac. | $C_{26}H_{25}N_3O_2$ (411.2) | 412 M + H⁺ |
| 33 | 2-(5-ethoxypyridyl) | 1st rac. | $C_{27}H_{27}N_3O_2$ (425.2) | 426 M + H⁺ |
| 34 | 2-(5-ethoxypyridyl) | 2nd rac. | $C_{27}H_{27}N_3O_2$ (425.2) | 426 M + H⁺ |
| 35 | 2-(5-ethoxypyridyl) | 3rd rac. | $C_{27}H_{27}N_3O_2$ (425.2) | 426 M + H⁺ |
| 36 | 2-(5-ethoxypyridyl) | 4th rac. | $C_{27}H_{27}N_3O_2$ (425.2) | 426 M + H⁺ |
| 37 | 2-(5-fluoropyridyl) | nonp. rac. | $C_{25}H_{22}FN_3O$ (399.2) | 400 M + H⁺ |
| 38 | 2-(5-fluoropyridyl) | pol. rac. | $C_{25}H_{22}FN_3O$ (399.2) | 400 M + H⁺ |
| 39 | 2-(5-chloropyridyl) | nonp. rac. | $C_{25}H_{22}ClN_3O$ (415.1) | 416 (418) M + H⁺ |
| 40 | 2-(5-chloropyridyl) | pol. rac. | $C_{25}H_{22}ClN_3O$ (415.1) | 416 (41) M + H⁺ |
| 41 | 2-(methyl pyridyl-5-carboxylate) | nonp. rac. | $C_{27}H_{25}N_3O_2$ (439.2) | 440.1 M + H⁺ |
| 42 | 2-(methyl pyridyl-5-carboxylate) | pol. rac. | $C_{27}H_{25}N_3O_2$ (439.2) | 440.1 M + H⁺ |
| 43 | 2-(pyridyl-5-carboxylic acid) | nonp. rac. | $C_{26}H_{23}N_3O_3$ (425.2) | 426.2 M + H⁺ |
| 44 | 2-(pyridyl-5-carboxylic acid) | pol. rac. | $C_{26}H_{23}N_3O_3$ (425.2) | 426.2 M + H⁺ |
| 45 | 2-(pyridyl-5-carboxylic acid) | | $C_{26}H_{24}N_4O_2$ (424.2) | 425 M + H⁺ |
| 46 | 3-hydroxyphenyl | nonp. rac. | $C_{26}H_{24}N_2O_2$ (396.2) | 397 M + H⁺ |
| 47 | 3-hydroxyphenyl | pol. rac. | $C_{26}H_{24}N_2O_2$ (396.2) | 397 M + H⁺ |
| 48 | methyl phenyl-2-carboxylate | nonp. rac. | $C_{28}H_{26}N_2O_3$ (438.2) | 439.2 M + H⁺ |
| 49 | methyl phenyl-2-carboxylate | pol. rac. | $C_{26}H_{26}N_2O_3$ (438.2) | 439.2 M + H⁺ |
| 50 | phenyl-2-carboxylic acid | | $C_{27}H_{24}N_2O_3$ (424.2) | 425.2 M + H⁺ |

TABLE 3

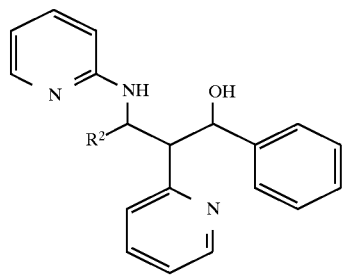

| Example | R² | | Empirical formula (molecular mass) | MS (FAB) |
|---|---|---|---|---|
| 51 | 2-nitrophenyl | nonp. rac. | $C_{25}H_{22}N_4O_3$ (426.2) | 427.2 M + H⁺ |
| 52 | 2-nitrophenyl | pol. rac. | $C_{25}H_{22}N_4O_3$ (426.2) | 427.2 M + H⁺ |
| 53 | 3-nitrophenyl | nonp. rac. | $C_{25}H_{22}N_4O_3$ (426.2) | 427.2 M + H⁺ |
| 54 | 3-nitrophenyl | pol. rac. | $C_{25}H_{22}N_4O_3$ (426.2) | 427.2 M + H⁺ |
| 55 | 3-nitrophenyl | (−)-enantiomer of Ex. 53 | $C_{25}H_{22}N_4O_3$ (426.2) | 427.2 M + H⁺ |
| 56 | 3-nitrophenyl | (+)-enantiomer of Ex. 53 | $C_{25}H_{22}N_4O_3$ (426.2) | 427.2 M + H⁺ |
| 57 | 4-nitrophenyl | nonp. rac. | $C_{25}H_{22}N_4O_3$ (426.2) | 427.1 M + H⁺ |
| 58 | 4-nitrophenyl | pol. rac. | $C_{25}H_{22}N_4O_3$ (426.2) | 427.1 M + H⁺ |
| 59 | 2-aminophenyl | nonp. rac. | $C_{25}H_{24}N_4O$ (396.2) | 397.2 M + H⁺ |
| 60 | 2-aminophenyl | pol. rac. | $C_{25}H_{24}N_4O$ (396.2) | 397.2 M + H⁺ |
| 61 | 2-aminophenyl | (−)-enantiomer of Ex. 59 | $C_{25}H_{24}N_4O$ (396.2) | 397.2 M + H⁺ |
| 62 | 2-aminophenyl | (+)-enantiomer of Ex. 59 | $C_{25}H_{24}N_4O$ (396.2) | 397.2 M + H⁺ |
| 63 | 3-aminophenyl | nonp. rac. | $C_{25}H_{24}N_4O$ (396.2) | 397.3 M + H⁺ |
| 64 | 3-aminophenyl | pol. rac. | $C_{25}H_{24}N_4O$ (396.2) | 397.2 M + H⁺ |
| 65 | 4-aminophenyl | nonp. rac. | $C_{25}H_{24}N_4O$ (396.2) | 397.3 M + H⁺ |
| 66 | 4-aminophenyl | pol. rac. | $C_{25}H_{24}N_4O$ (396.2) | 397.2 M + H⁺ |
| 67 | 2-hydroxyphenyl | nonp. rac. | $C_{25}H_{23}N_3O_2$ (397.2) | 398.2 M + H⁺ |
| 68 | 2-hydroxyphenyl | pol. rac. | $C_{25}H_{23}N_3O_2$ (397.2) | 398 M + H⁺ |
| 69 | 2-hydroxyphenyl | (+)-enantiomer of Ex. 67 | $C_{25}H_{23}N_3O_2$ (397.2) | 398 M + H⁺ |
| 70 | 2-hydroxyphenyl | (−)-enantiomer of Ex. 67 | $C_{25}H_{23}N_3O_2$ (397.2) | 398 M + H⁺ |
| 71 | 3-hydroxyphenyl | nonp. rac. | $C_{25}H_{23}N_3O_2$ (397.2) | 398 M + H⁺ |
| 72 | 3-hydroxyphenyl | pol. rac. | $C_{25}H_{23}N_3O_2$ (397.2) | 398 M + H⁺ |
| 73 | 4-hydroxyphenyl | nonp. rac. | $C_{25}H_{23}N_3O_2$ (397.2) | 398 M + H⁺ |
| 74 | 4-hydroxyphenyl | pol. rac. | $C_{25}H_{23}N_3O_2$ (397.2) | 398 M + H⁺ |
| 75 | 2-benzyloxyphenyl | nonp. rac. | $C_{32}H_{29}N_3O_2$ (487.2) | 488 M + H⁺ |
| 76 | 2-benzyloxyphenyl | pol. rac. | $C_{32}H_{29}N_3O_2$ (487.2) | 488 M + H⁺ |
| 77 | 4-acetoxyphenyl | nonp. rac. | $C_{27}H_{25}N_3O_3$ (439.1) | 440 M + H⁺ |
| 78 | 4-acetoxyphenyl | pol. rac. | $C_{27}H_{25}N_3O_3$ (439.1) | 440 M + H⁺ |

TABLE 4

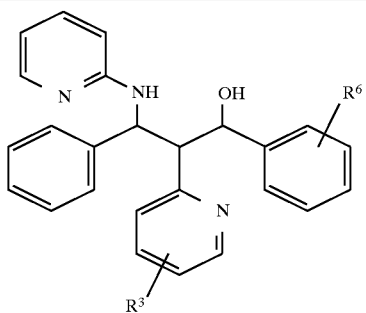

| Example | R³ | R⁶ | | Empirical formula (molecular mass) | MS (FAB) |
|---|---|---|---|---|---|
| 79 | 4-methoxy | H | nonp. rac. | $C_{26}H_{25}N_3O_2$ (411.2) | 412 M + H⁺ |
| 80 | 4-methoxy | H | pol. rac. | $C_{26}H_{25}N_3O_2$ (411.2) | 412 M + H⁺ |
| 81 | H | 3-hydroxy | nonp. rac. | $C_{25}H_{23}N_3O_2$ (397.2) | 398 M + H⁺ |
| 82 | H | 4-hydroxy | nonp. rac. | $C_{25}H_{23}N_3O_2$ (397.2) | 398 M + H⁺ |
| 83 | H | 3-methoxy | nonp. rac. | $C_{26}H_{25}N_3O_2$ (411.2) | 412 M + H⁺ |
| 84 | H | 3-methoxy | pol. rac. | $C_{26}H_{25}N_3O_2$ (411.2) | 412 M + H⁺ |
| 85 | H | 4-methoxy | nonp. rac. | $C_{26}H_{25}N_3O_2$ (411.2) | 412 M + H⁺ |
| 86 | H | 4-methoxy | pol. rac. | $C_{26}H_{25}N_3O_2$ (411.2) | 412 M + H⁺ |
| 87 | H | 4-amino | nonp. rac. | $C_{25}H_{24}N_4O$ (396.2) | 397 M + H⁺ |
| 88 | H | 4-amino | pol. rac. | $C_{25}H_{24}N_4O$ (396.2) | 397 M + H⁺ |

TABLE 4-continued

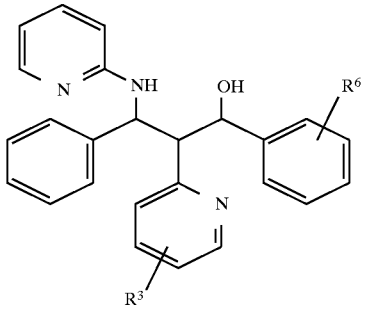

| Example | $R^3$ | $R^6$ | | Empirical formula (molecular mass) | MS (FAB) |
|---|---|---|---|---|---|
| 89 | H | 4-benzyloxycarbonylamido | nonp. rac. | $C_{33}H_{30}N_4O_3$ (530.2) | 531 M + H$^+$ |
| 90 | H | 4-benzyloxycarbonylamido | pol. rac. | $C_{33}H_{30}N_4O_3$ (530.2) | 531 M + H$^+$ |

TABLE 5

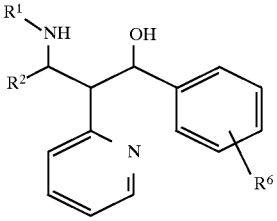

| Example | $R^1$ | $R^2$ | $R^6$ | Empirical formula (molecular mass) | MS (FAB) |
|---|---|---|---|---|---|
| 91 | pyridyl | 2-aminophenyl | 4-methoxy | $C_{26}H_{26}N_4O_2$ (426.2) | 427 M + H$^+$ |
| 92 | pyridyl | 2-nitro-5-hydroxyphenyl | H | $C_{25}H_{22}N_4O_4$ (442.2) | 443.1 M + H$^+$ |
| 93 | pyridyl | 2-amino-5-hydroxyphenyl | H | $C_{25}H_{22}N_4O_4$ (412.2) | 413.2 M + H$^+$ |
| 94 | 3,5-bis(trifluoromethyl)phenyl | phenyl | H | $C_{28}H_{22}F_6NO$ | |

| Example | Structure | Empirical formula (molecular mass) | MS (FAB) |
|---|---|---|---|
| 95 | 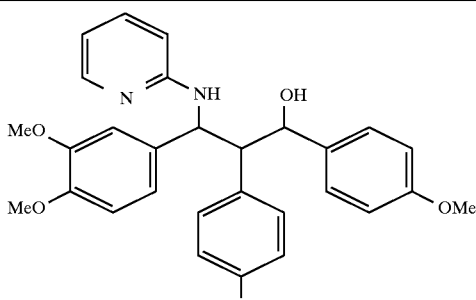 | $C_{30}H_{32}N_2O_5$ (500.2) | 501 M + H$^+$ |

EXAMPLE 97

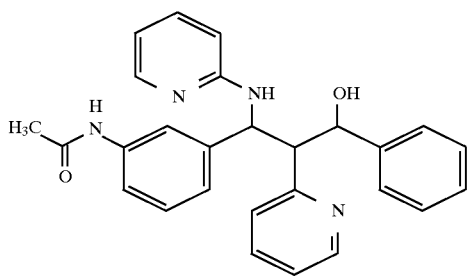

300 mg (0.76 mmol) of amino compound from Example 63 were dissolved in 10 ml of pyridine, treated with 75 μl (0.80 mmol) of acetic anhydride and 5 mg of dimethylaminopyridine and stirred at room temperature for 2 h. 30 ml of water were then added and the mixture was extracted 3× with ethyl acetate. The organic phases were dried and concentrated. Silica gel chromatography using n-heptane/ethyl acetate 4:1 afforded 200 mg (60%) of product. $C_{27}H_{26}N_4O_2$ (438.2) MS (FAB) 439.2 M+H$^+$

EXAMPLE 98

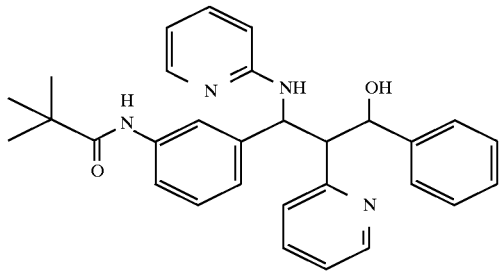

In analogy to Example 97, the compound indicated above was obtained using pivaloyl chloride.

$C_3OH_{32}N_4O_2$ (480.3) MS (FAB) 481.3 M+H$^+$

EXAMPLE 99

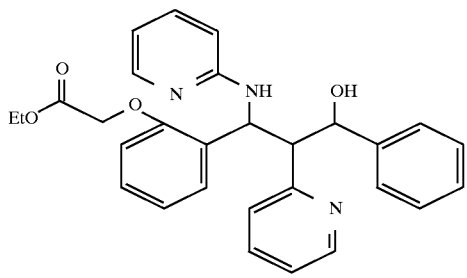

1.99 g (0.005 mol) of Example 67 and 1 g of powdered potassium carbonate were initially introduced into 50 ml of dimethylformamide. 0.7 ml (0.006 mol) of ethyl bromoacetate was added to the solution and it was heated under reflux for 6 h. It was then concentrated in vacuo and the residue was chromatographed on silica gel using n-heptane/ethyl acetate 2:1. Yield 1.94 g (80%)

$C_{29}H_{29}N_3O_4$ (483) MS (FAB) 484 M+H$^+$

EXAMPLE 100

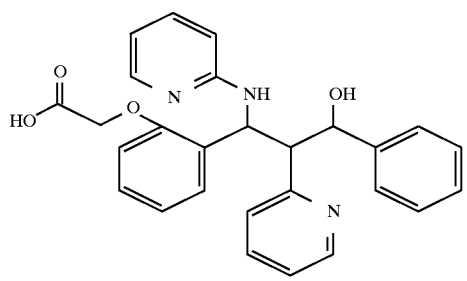

Example 100 was prepared from Example 99 by the process described for Example 4.

$C_{27}H_{25}N_3O_4$ (455) MS (FAB) 456 M+H$^+$

EXAMPLE 101

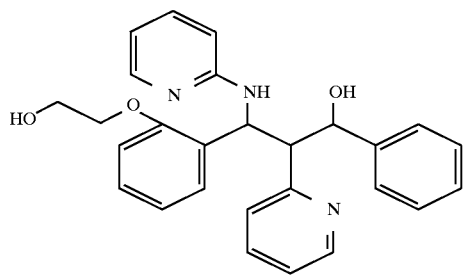

1.99 g (0.005 mol) of Example 67 and 8.8 g (0.1 mol) of ethylene carbonate were heated to 90°–95° C. in an oil bath (melt). At this temperature, 0.14 g (0.001 mol) of potassium carbonate were added and the mixture was stirred for 5 h. After cooling, the solution obtained was filtered and concentrated in vacuo. Chromatography on silica gel using n-heptane/ethyl acetate 1:1 afforded 1.5 g (68%) of product.

$C_{27}H_{27}N_3O_3$ (441) MS (FAB) 442 M+H$^+$

EXAMPLE 102

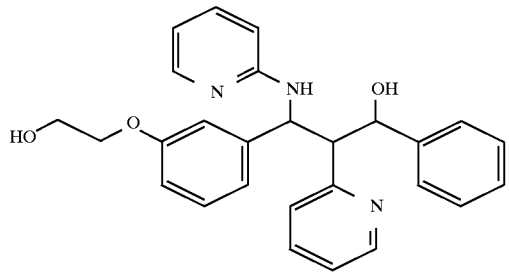

Example 102 was obtained from Example 71 analogously to the process described for Example 101.

$C_{27}H_{27}N_3O_3$ (441) MS (FAB) 442 M+H$^+$

EXAMPLE 103

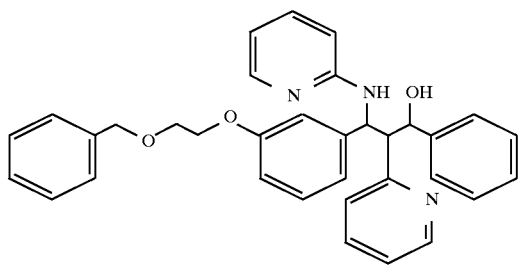

4.04 g (20 mmol) of diisopropyl azodicarboxylate and then 3.97 g (10 mmol) of Example 71 were added under argon to a solution of 1.83 g (12 mmol) of benzyloxyethanol and 3.67 g (14 mmol) of triphenylphosphine in 100 ml of dry THF. After stirring overnight, the solvent was removed and the residue was again dissolved in ethyl acetate. This solution was extracted 2× by shaking with $Na_2CO_3$ solution, then dried and concentrated. Silica gel chromatography afforded 3.85 g (72%) of product.

$C_{34}H_{33}N_3O_3$ (531.3) MS (FAB) 532 M+H$^+$

| Ex. | Structure | Empirical formula (molecular mass) Comment | MS |
|---|---|---|---|
| 104 | 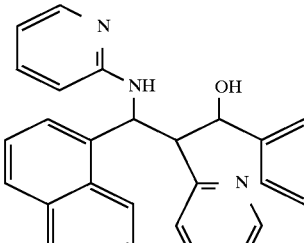 | $C_{29}H_{25}N_3O$ (431.54) nonpolar rac. | 432 (M + 1) |
| 105 | 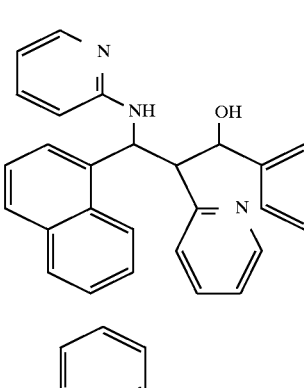 | $C_{29}H_{25}N_3O$ (431.54) polar rac. | 432 (M + 1) |
| 106 | 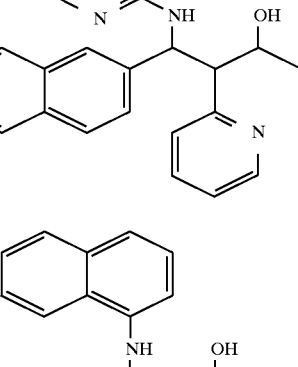 | $C_{29}H_{25}N_3O$ (431.54) polar rac. | 432 (M + 1) |
| 107 | 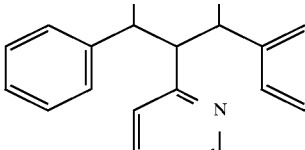 | $C_{30}H_{26}N_2O$ (430.55) nonpolar rac. | 421 (M + 1) |

-continued

| Ex. | Structure | Empirical formula (molecular mass) Comment | MS |
|---|---|---|---|
| 108 | 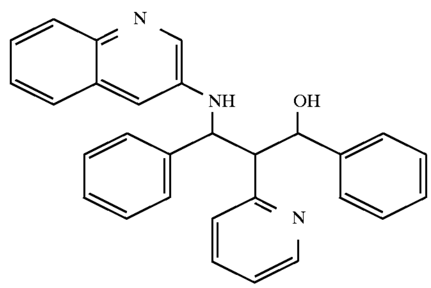 | $C_{29}H_{25}N_3O$ (431.54) nonpolar rac. | 432 (M + 1) |
| 109 | 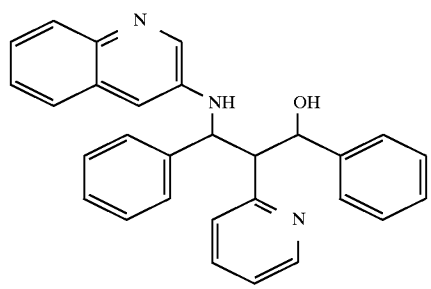 | $C_{29}H_{25}N_3O$ (431.54) medium-polar rac. | 432 (M + 1) |
| 110 | 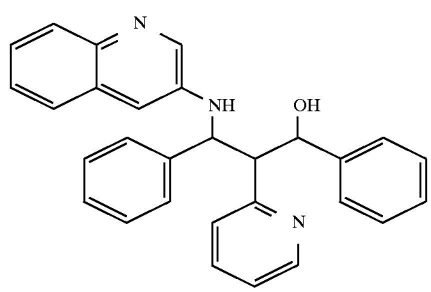 | $C_{29}H_{25}N_3O$ (431.54) polar rac. | 432 (M + 1) |
| 111 | 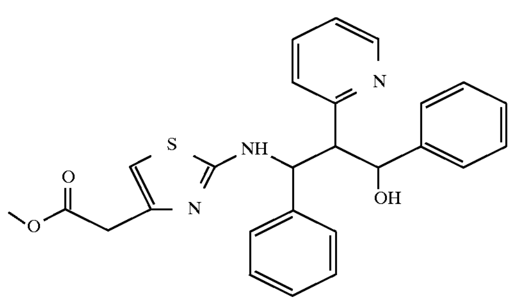 | $C_{26}H_{25}N_3O_3S$ (431.54) polar rac. | 432 (M + 1) |
| 112 | 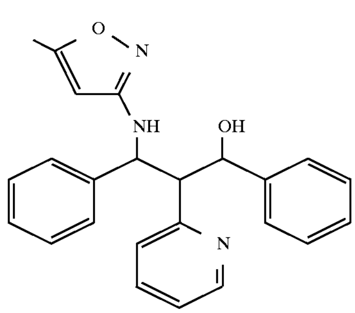 | $C_{24}H_{23}N_3O_2$ (385.47) nonpolar rac. | 386 (M + 1) |

-continued
| Ex. | Structure | Empirical formula (molecular mass) Comment | MS |
|---|---|---|---|
| 113 | 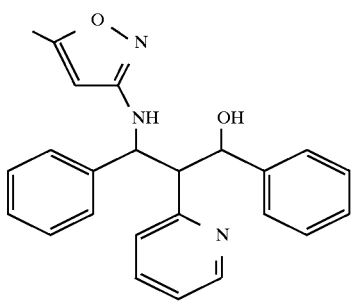 | $C_{24}H_{23}N_3O_2$ (385.47) medium-polar rac. | 386 (M + 1) |
| 114 | 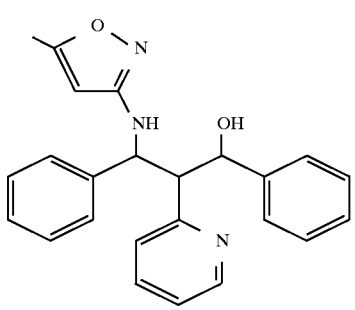 | $C_{24}H_{23}N_3O_2$ (385.47) polar rac. | 386 (M + 1) |
| 115 | 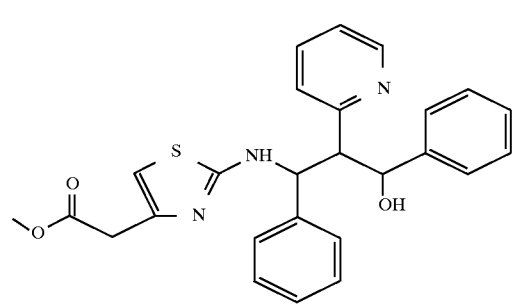 | $C_{26}H_{25}N_3O_3S$ (459.57) nonpolar rac. | 460 (M + 1) |
| 116 | 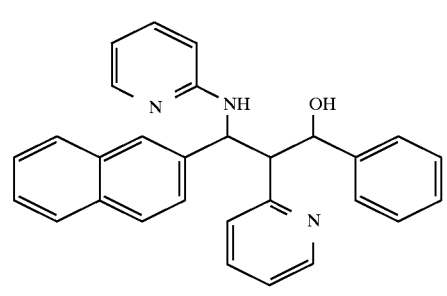 | $C_{29}H_{25}N_3O$ (431.54) nonpolar rac. | 432 (M + 1) |
| 117 | 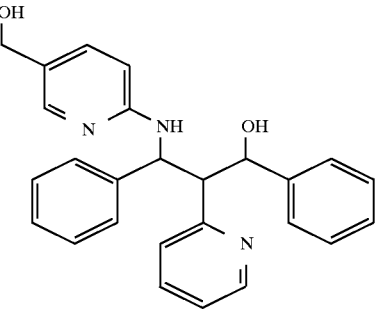 | $C_{26}H_{25}N_3O_2$ (411.51) more strongly polar rac. | 412 (M + H$^+$) |

-continued

| Ex. | Structure | Empirical formula (molecular mass) Comment | MS |
|---|---|---|---|
| 118 | 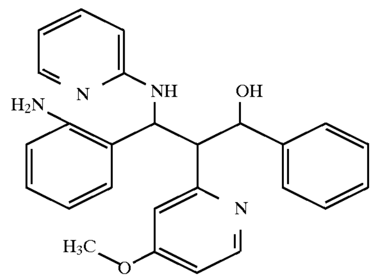 | $C_{26}H_{25}N_4O_2$ (426.52) nonpolar rac. | 427 (M + H$^+$) |
| 119 | 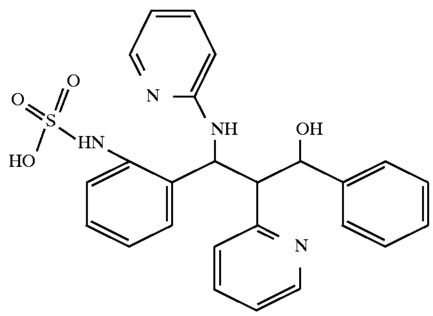 | $C_{25}H_{24}N_4O_4S$ (476.56) stereoisomer mixture | 477 (M + H$^+$) |
| 120 | 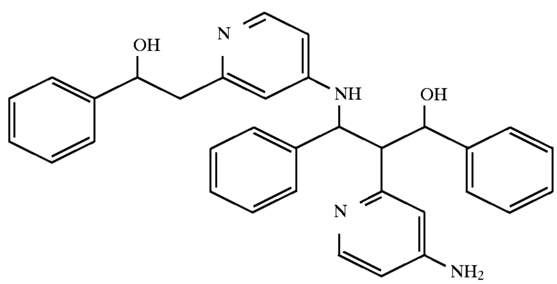 | $C_{33}H_{32}N_4O_2$ (516.65) stereoisomer mixture | 515 (M + H$^+$) |
| 121 | 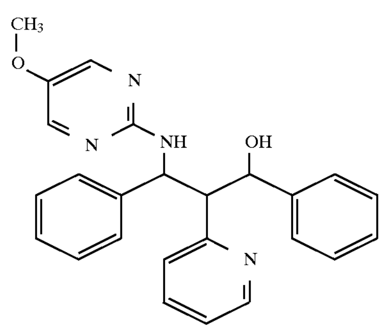 | $C_{25}H_{24}N_4O_2$ (412.5) less polar rac. | 413 (M + H$^+$) |
| 122 | 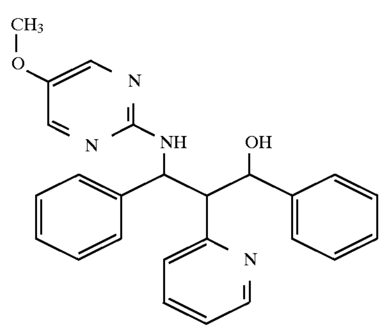 | $C_{25}H_{24}N_4O_2$ (412.5) more strongly polar rac. | 413 (M + H$^+$) |

-continued
| Ex. | Structure | Empirical formula (molecular mass) Comment | MS |
|---|---|---|---|
| 123 | 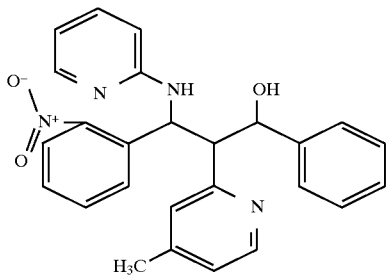 | $C_{26}H_{24}N_4O_3$ (440.51) less strongly polar rac. | 441 (M + H$^+$) |
| 124 | 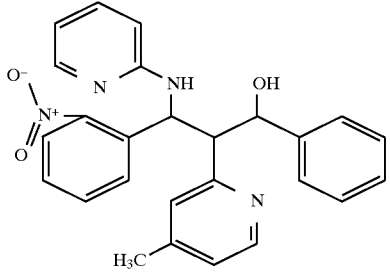 | $C_{26}H_{24}N_4O_3$ (440.51) more strongly polar rac. | 441 (M + H$^+$) |
| 125 | 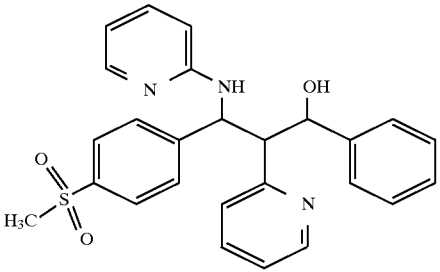 | $C_{26}H_{25}N_3O_3S$ (459.57) less strongly polar rac. | 460 (M + H$^+$) |
| 126 | 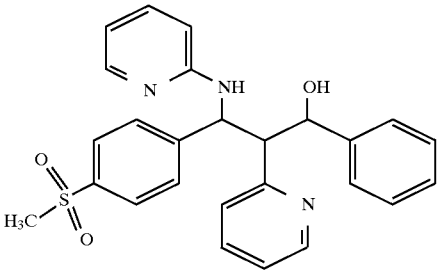 | $C_{26}H_{25}N_3O_3S$ (459.57) more strongly polar rac. | 460 (M + H$^+$) |
| 127 | 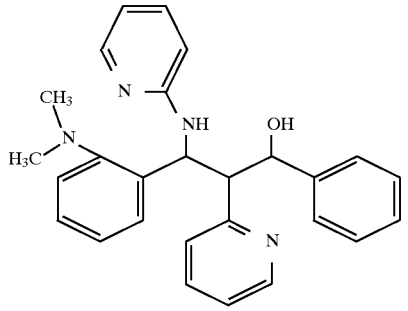 | $C_{27}H_{28}N_4O$ (424.55) less strongly polar rac. | 425 (M + H$^+$) |

We claim:
1. A propanolamine derivative of formula I,

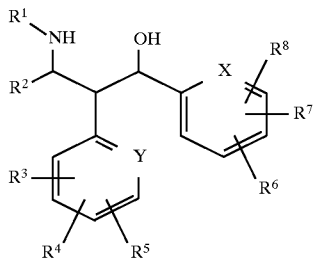

or a physiologically tolerable acid addition salt thereof;
in which $R^1$ and $R^2$ each independently represent cycloalkyl having 3–8 ring carbon atoms, phenyl, naphthyl, phenanthryl, pyridyl, thienyl, furyl, pyrimidyl, indolyl, thiazolyl, imidazolyl, coumarinyl, phthalimidyl, quinolyl, piperazinyl, tetrazolyl, triazolyl, oxazolyl or their thieno-, pyridino- or benzo-fused derivatives, wherein the cycloalkyl ring, aromatic ring or heteroaromatic ring can be mono- to tri-substituted by fluorine, chlorine, bromine, iodine, —OH, —CF$_3$, —NO$_2$, —CN, (C$_1$–C$_8$)-alkoxy, (C$_1$–C$_8$)-alkyl, —NH$_2$, —NH—R$^9$, —N(R$^9$)R$^{10}$, CHO, —COOH, —COOR$^{11}$, —(C=O)—R$^{12}$, (C$_1$–C$_6$)-alkyl-OH, (C$_1$–C$_6$)-alkyl(-OH)-phenyl, (C$_1$–C$_6$)-alkyl-CF$_3$, (C$_1$–C$_6$)-alkyl-NO$_2$, (C$_1$–C$_6$)-alkyl-CN, (C$_1$–C$_6$)-alkyl-NH$_2$, (C$_1$–C$_6$)-alkyl-NH—R$^9$, (C$_1$–C$_6$)-alkyl-N(R$^9$)R$^{10}$, (C$_1$–C$_6$)-alkyl-CHO, (C$_1$–C$_6$)-alkyl-COOH, (C$_1$–C$_6$)-alkyl-COOR$^{11}$, (C$_1$–C$_6$)-alkyl-(C=O)—R$^{12}$, —O—(C$_1$–C$_6$)-alkyl-OH, —O—(C$_1$–C$_6$)-alkyl-CF$_3$, —O—(C$_1$–C$_6$)-alkyl-NO$_2$, —O—(C$_1$–C$_6$)-alkyl-CN, —O—(C$_1$–C$_6$)-alkyl-NH$_2$, —O—(C$_1$–C$_6$)-alkyl-NH—R$^9$, —O—(C$_1$–C$_6$)-alkyl-N($^9$)R$^{10}$, —O—(C$_1$–C$_6$)-alkyl-CHO, —O—(C$_1$–C$_6$)-alkyl-COOH, —O—(C$_1$–C$_6$)-alkyl-COOR$^{11}$, —O—(C$_1$–C$_6$)-alkyl-(C=O)—R$^{12}$, —N—SO$_3$H, —SO$_2$—CH$_3$, —O—(C$_1$–C$_6$)-alkyl-O—(C$_1$–C$_6$)-alkylphenyl, wherein one or more hydrogens of the alkyl radicals of these substituents can be replaced by fluorine;

$R^3$ to $R^8$ each independently represent hydrogen, fluorine, chlorine, bromine, iodine, —OH, —CF$_3$, —NO$_2$, —CN, (C$_1$–C$_8$)-alkoxy, (C$_1$–C$_8$)-alkyl, —NH$_2$, —NH—R$^9$, —N(R$^9$)R$^{10}$, —CHO, —COOH, —COOR$^{11}$, —(C=O)—R$^{12}$, wherein one or more hydrogens of the alkyl radicals of these substituents can be replaced by fluorine;

$R^9$ to $R^{12}$ each independently represent hydrogen, (C$_1$–C$_8$)-alkyl;

X is CH or NH;

Y is CH or NH;

with the proviso that the radicals $R^1$, $R^2$, X and Y do not simultaneously have the following meaning:

$R^1$ is phenyl;
$R^2$ is phenyl;
X is CH;
Y is CH.

2. A compound of formula I of claim 1, wherein $R^1$ and $R^2$ each independently represent cycloalkyl having 3–8 ring carbon atoms, phenyl, naphthyl, thienyl, furyl, pyrimidyl, thiazolyl, imidazolyl, phthalimidyl, quinolyl, piperazinyl, tetrazolyl, triazolyl, oxazolyl or their thieno-, pyridino- or benzo-fused derivatives, wherein the cycloalkyl ring, aromatic ring or heteroaromatic ring can be mono- to tri-substituted by fluorine, chlorine, bromine, —OH, —CF$_3$, —NO$_2$, —CN, (C$_1$–C$_8$)-alkoxy, (C$_1$–C$_8$)-alkyl, —NH$_2$, —NH—R$^9$, —N(R$^9$)R$^{10}$, —COOH, —COOR$^{11}$, —(C=O)—R$^{12}$, wherein one or more hydrogens of the alkyl radicals of these substituents can be replaced by fluorine;

$R^3$ to $R^8$ each independently represent hydrogen, fluorine, chlorine, bromine, —OH, —CF$_3$, —NO$_2$, —CN, (C$_1$–C$_8$)-alkoxy, (C$_1$–C$_8$)-alkyl, —NH$_2$, —NH—R$^9$, —N(R$^9$)R$^{10}$, —COOH, —COOR$^{11}$, —(C=O)—R$^{12}$, wherein one or more hydrogens of the alkyl radicals of these substituents can be replaced by fluorine.

3. A compound of formula I as claimed in claim 1, wherein $R^1$ is pyridyl, pyrimidyl, thienyl, or thiazolyl, wherein the heteroaromatic ring can be mono- to tri-substituted by fluorine, chlorine, bromine, iodine, —OH, —CF$_3$, —NO$_2$, —CN, (C$_1$–C$_8$)-alkoxy, (C$_1$–C$_8$)-alkyl, —NH$_2$, —NH—R$^9$, —N(R$^9$)R$^{10}$, CHO, —COOH, —COOR$^{11}$, —(C=O)—R$^{12}$;

$R^2$ is phenyl, wherein said phenyl can be mono- to tri-substituted by fluorine, chlorine, bromine, —OH, —CF$_3$, —NO$_2$, —CN, (C$_1$–C$_8$)-alkoxy, (C$_1$–C$_8$)-alkyl, NH$_2$, —NH—R$^9$, —N(R$^9$)R$^{10}$, —COOH, —COOR$^{11}$, —(C=O)—R$^{12}$;

$R^3$ to $R^8$ each independently represent hydrogen, fluorine, chlorine, bromine, iodine, —OH, —CF$_3$, —NO$_2$, —CN, (C$_1$–C$_8$)-alkoxy, (C$_1$–C$_8$)-alkyl, —NH$_2$, —NH—R$^9$, —N(R$^9$)R$^{10}$, —CHO, —COOH, —COOR$^{11}$, —(C=O)—R$^{12}$, wherein one or more hydrogens of the alkyl radicals of these substituents can be replaced by fluorine;

X is CH; and

Y is NH.

4. A process for preparing a compound of formula I of claim 1, which comprises steps according to the following reaction scheme

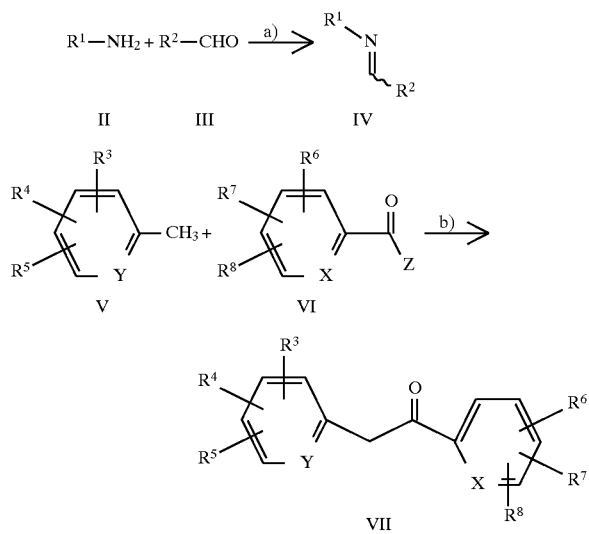

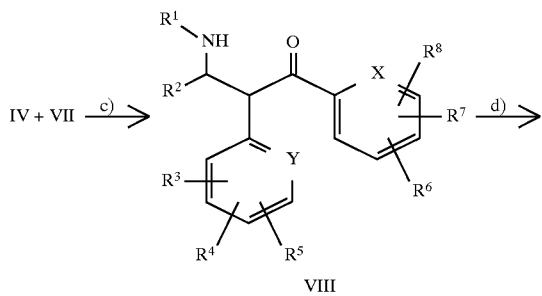

VIII

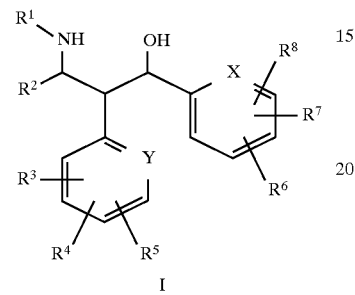

I a) preparing an imine of formula V, in which $R^1$ and $R^2$ have the meaning indicated for formula I by reacting an amine of formula II with an aldehyde of formula III, and b) preparing a keto compound of formula VII in which X, Y and $R^3$ to $R^8$ have the meaning indicated for formula I by reacting a compound of formula V with a compound of formula VI, and c) preparing a compound of formula VIII in which X, Y and $R^1$ to $R^8$ have the meanings indicated for formula I by reacting a compound of formula IV with a compound of formula VII, and d) reducing the compound of formula VIII in a suitable solvent at a temperature from −30° C. to +40° C. using a suitable reductant to give a compound of formula I.

5. A process of claim 4, further comprising converting the compound of formula I to a physiologically tolerable acid addition salt.

6. A process for the preparation of a compound of formula I of claim 1, which comprises steps according to the following reaction scheme

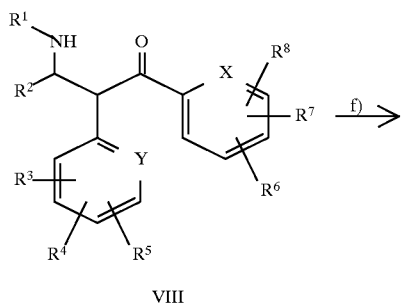

VIII e) reacting the compounds of formula II ($R^1$—$NH_2$), formula III ($R^2$—CHO), and formula VII

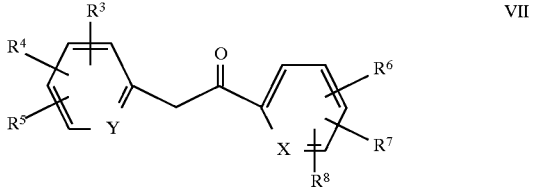

in a suitable solvent at a temperature from 20° C. to 150° C. to give a compound of formula VIII, and f) reducing the compound of formula VIII in a suitable solvent at a temperature from −30° C. to +40° C. using a suitable reductant to give a compound of formula I, wherein $R^1$–$R^8$, X, and Y are defined as in claim 1.

7. A process of claim 6, further comprising converting the compound of formula I to a physiologically tolerable acid addition salt.

8. A pharmaceutical composition, comprising at least one compound of claim 1 and a pharmaceutically acceptable carrier.

9. The pharmaceutical composition of claim 8, further comprising at least one hypolipidemic active compound.

10. A method for treating lipid metabolism disorders, comprising administering to a host in need thereof an effective amount of a compound of formula I of claim 1.

11. A method for treating hyperlipidemia, comprising administering to a host in need thereof an effective amount of a compound of formula I of claim 1.

12. A method for affecting the serum cholesterol level of a host, comprising administering to a host in need thereof an effective amount of a compound of formula I of claim 1.

13. A method for preventing arteriosclerotic symptoms, comprising administering to a host in need thereof an effective amount of a compound of formula I of claim 1.

14. A pharmaceutical composition for treating lipid metabolism disorders, comprising an effective amount of a compound of formula I of claim 1 and a pharmaceutically acceptable carrier.

15. A pharmaceutical composition for treating hyperlipidemia, comprising an effective amount of a compound of formula I of claim 1 and a pharmaceutically acceptable carrier.

16. A pharmaceutical composition for affecting serum cholesterol level, comprising an effective amount of a compound of formula I of claim 1 and a pharmaceutically acceptable carrier.

17. A pharmaceutical composition for preventing arteriosclerotic symptoms, comprising an effective amount of a compound of formula I of claim 1 and a pharmaceutically acceptable carrier.

* * * * *